United States Patent [19]

Udvardy Nagy née Cserey Pechány et al.

[11] Patent Number: 4,528,271

[75] Date of Patent: Jul. 9, 1985

[54] PROCESS FOR THE INTENSIFICATION OF MICROBIOLOGICAL CONVERSIONS OF STEROIDS USING CYCLODEXTRIN ADDITIVES

[75] Inventors: Éva Udvardy Nagy née Cserey Pechány; István Bartho; Gábor Hantos; Mária Trinn; Zsuzsa Vida; József Szejtli; Agnes Stadler née Szöke; Ilona Habon; Márta Balázs née Czurda, all of Budapest, Hungary

[73] Assignees: Richter Gedeon Vegyeszeti Gyar Rt.; Chinoin Gyogyszer- Es Vegyeszeti Termekek Gyara Rt., both of Budapest, Hungary

[21] Appl. No.: 423,084

[22] Filed: Sep. 24, 1982

[30] Foreign Application Priority Data

Sep. 28, 1981 [HU] Hungary ................................. 2785

[51] Int. Cl.³ ...................... C12P 33/16; C12P 33/00; C12P 33/20; C12P 33/12; C12P 33/18; C12P 33/14; C12P 33/06; C12P 33/08; C12P 33/10; C12P 33/02; C12P 33/04
[52] U.S. Cl. ......................................... 435/55; 435/52; 435/53; 435/54; 435/56; 435/57; 435/58; 435/59; 435/60; 435/61; 435/62
[58] Field of Search ..................... 435/52, 53, 54, 55, 435/56, 57, 58, 59, 60, 61, 62

[56] References Cited

U.S. PATENT DOCUMENTS 3,639,212  2/1972  Shirasaka et al. .................... 435/62
4,057,469  11/1977  Nishikawa et al. .................. 435/55
4,397,946  8/1983  Imada et al. ......................... 435/55

FOREIGN PATENT DOCUMENTS 176250  6/1981  Hungary .
2034716  1/1983  United Kingdom .

OTHER PUBLICATIONS

Applied Microbiology, 1972, 23(1), 72–77.
Helv. Chim. Acts., 1954, 37, 1548–15553.

Primary Examiner—Alvin E. Tanenholtz
Attorney, Agent, or Firm—Karl F. Ross; Herbert Dubno

[57] ABSTRACT

Microbiological conversions of cyclodextrins are intensified by adding to the reaction mixture 0.2 to 3 moles of α-, β- or γ-cyclodextrin or an optical mixture thereof pro mole of the steroid substrate, before, at the beginning or during the conversion. The cyclodextrin if desired, can be removed after the reaction. In this way the reaction velocity can be increased, the reaction time is reduced, the substrate concentration in the solution, i.e. its solubility is increased or the so called product inhibition may be avoided. In certain cases of more alternatives the desired reaction can be catalyzed and in this manner the selectivity is increased.

14 Claims, No Drawings

PROCESS FOR THE INTENSIFICATION OF MICROBIOLOGICAL CONVERSIONS OF STEROIDS USING CYCLODEXTRIN ADDITIVES

This invention relates to a process for the intensification of microbiological conversions of steroids using cyclodextrin additives.

In the synthesis of steroid compounds certain reaction steps are often carried out by means of microorganisms. The bioconversions employing microorganism cells, enzymes extracted therefrom or fixed cells or enzymes are performed in an aqueous medium. This facilitates the progress of enzymatic reactions, but at the same time is, however, disadvantageous due to the poor solubility of steroids in water. There are numerous steroids which are so poorly soluble in water that their bioconversions cannot be economically carried out in an aqueous medium.

In the known procedures a portion of the substrate and the product steroids is generally in a solid state during the reaction. In such cases the reaction velocity may be determined by the dissolution of the substrate and if the grain size is heterogenous, i.e. the mean grain size is gradually increasing during the progress of the reaction, the velocity is continuously decreasing. Due to such and similar problems the reaction frequently terminates before the desired conversion grade.

There are more processes known in the art for the improvement of water-solubility of the steroid substrates or for the acceleration of the velocity of their dissolution. According to the British Patent Specification No. 1 211 356 the steroid to be subjected to conversion is previously mechanically dispersed to ensure a homogenous grain distribution and a small average grain size.

According to the U.S. Pat. No. 4,124,607 a finely divided substrate is prepared in a separate step by emulsifying an organic solution of a steroid in water and subsequently evaporating the organic solvent. Other authors suggest to dissolve the steroids in an organic solvent, to add the organic solution to the aqueous medium of the bioconverion wherein the substrate precipitates in a finely divided form.

According to the Hungarian Patent Specification No. 149 678 the organic solvent used for the introduction of the substrate (e.g. pyridine, acetic acid) is neutralized prior to bioconversion. In the case of alcohols the dissolution is increased by adding alkali earth metal chlorides.

According to the British Patent Specification No. 1 083 204 the solubility of the substrates in an aqueous medium is increased by organic solvents, in particular dimethyl sulfoxide. The organic auxiliary solvent may be added simultaneously with the addition of substrate or subsequently. Alternatively, the water-solubility of the substrates can be increased by water-immiscible solvents, when the high interface of the emulsion formed ensures a quick material transport [Biotechn. Bioeng. 21, 39 (1979)]. Solubilizing agents are frequently used in the pharmaceutical industry. For instance according to the German Patent Specification No. 1 543 431 in the preparation of androstene-dione from 4-collesten-3-one the yield has considerably been increased by employing solubilizing agents.

Though the known processes decrease the disadvantages due to the poor water-solubility of substrates, they have other disadvantageous effects on the system or are uneconomic. If, for example, a substrate is prepared in a microcrystalline form, this requires an additional operation and results in material loss. It has further been observed that the organic solvents in an amount required to increase the solubility of steroids sufficiently are detrimental to the microorganisms [Steroids, 12, 525 (1968)]. The solubilizing agents generally accelerate foaming which renders the aeration of the bioconversion system difficult.

The invention relates to a process by which the microbiological conversion of steroids can efficiently be intensified while the disadvantages of the prior art can be avoided or at least diminished.

We have surprisingly found that in bioconversion systems the cyclodextrins can successfully be employed to increase the water-solubility of steroid molecules, in the case of a solid residue to increase the velocity of dissolution, to avoid the "product inhibition" hindering the progress of the reaction and in certain cases to suppress side reactions. In addition, $\alpha$- and $\beta$-cyclodextrins and optional mixtures thereof have a catalytic effect on ester hydrolysis. If the microorganisms have two or more functions, the selective effects can advantageously be used to influence the proportion of the reaction products.

The term "intensification" as used herein and throughout the specification and claims refers to the complex effects described hereinabove.

According to the invention a steroid substrate is reacted with a microorganism in the presence of an $\alpha$-, $\beta$- or $\gamma$-cyclodextrin or an optional mixture thereof and if desired, after the termination of the reaction the cyclodextrin is separated from the system. In the following, if not otherwise stated, the term "cyclodextrin" refers to $\alpha$-, $\beta$- or $\gamma$-cyclodextrin or an optional mixture thereof.

The cyclodextrin can be added before the microbiological reaction, at the start or at optional stages thereof, in an amount of 0.2 to 3 moles of cyclodextrin per 1 mole of substrate.

According to a preferred embodiment of the invention the cyclodextrin is added to the medium of bioconverion prior to the addition of the substrate.

Alternetively, the cyclodextrin may be reacted with the substrate and the inclusion complex obtained or an aqueous solution or suspension thereof can be added to the medium of bioconversion.

According to a further embodiment the cyclodextrin is added in a certain stage of the reaction, preferably after a 30 to 50% conversion, as such, in the form of an inclusion complex with the steroid substrate or as an aqueous solution or suspension thereof. If desired, a solution of the cyclodextrin or the cyclodextrin-substrate inclusion complex can be sterilized prior to addition to the medium of bioconversion or the sterilization can be carried out together with the medium of bioconversion.

Cyclodextrin can be recovered from the aqueous medium of bioconversion by extracting the steroid with an organic solvent and subsequently precipitating the cyclodextrin from the raffinate by means of a solvent efficiently decreasing its solubility, preferably hexane. Cyclodextrin is then isolated by filtration and if desired, dried.

The intensification of microbiological conversions of steroids is of primary importance since as a result the reaction velocity is increased, the time required for the conversion is reduced, the substrate concentration is increased in the medium, the product inhibition is avoided and the desired reactions can be catalyzed selectively, i.e. the microbiological selection is increased.

The inclusion complexes of steroid substrates with cyclodextrins can be prepared in more alternative ways. According to the first variant an aqueous solution of the desired cyclodextrin having a suitable cyclodextrin concentration is used as a medium for bioconversion and the substrate steroid is added to this solution, in which an inclusion complex is formed corresponding to equilibrium state (variant 1).

Alternatively, an aqueous solution of the substrate-cyclodextrin inclusion complex is prepared separately and is subsequently added to the medium of biconversion, after sterilization by filtration (variant 2).

In the presence of a small amount of water the mixtures of steroids with cyclodextrins can be recrystallized to afford steroid-cyclodextrin complexes which can be added as a solid to bioconversions where sterilization is not required (variant 3).

Cyclodextrins are cyclic molecules consisting of 6, 7 or 8 glucopyranose units forming $\alpha$-1,4-glucose units. Structurally they are characterized by a special arrangement of the hydroxyl groups. All the secondary hydroxyls are situated on one edge of the ring, while all the primary hydroxyls are placed on the other edge of that ring. Therefore the outer surface of the ring is essentially hydrophilic which ensures that the cyclodextrins are water-soluble. On the other hand the inner surface of the rings has a hydrophobic character since in that part of the molecule only hydrogen atoms and glucosidal oxygen bridges are to be found. Consequently, molecules the shape and size of which enables them to penetrate into the cave inside the cyclodextrin form inclusion complexes with cyclodextrins. The ring consisting of 6 glucopyranose units is called $\alpha$-cyclodextrin, that consisting of 7 units is called $\beta$-cyclodextrin and finally the ring having 8 glucopyranose units is called $\gamma$-cyclodextrin. Cyclodextrins are sometimes called cycloamyloses as well.

Complexes of various pharmaceutically active steroid compounds with cyclodextrins were tested by Lech and Pauli [J. Pharm. Sci. 55, 32 (1966)]. For complexes of testosterone and cortisone acetate even the probable stochiometric ratios were determined. By the experiments the adsorption of the active substances was to be influenced via solubilization. There is, however, neither disclosure nor suggestion as to the intensification of the microbiological conversions of steroid substrates.

We have found that the complexes of steroid substrates with cyclodextrins dissociate in aqueous medium instantaneously and in a bioconversion system the complexes are in dinamical equilibrium with the free steroid and cyclodextrin molecules. In bioconversion systems, containing a solid suspended steroid the actual concentration of the dissolved steroid, i.e. of the steroid which is available to the enzyme depends on the velocity of the enzymatic reaction and of the dissolution of the substrate. If the dissolution of the substrate is a slower process, the concentration of the steroid in the solution remains considerably under the saturation value and accordingly, the velocity of the enzyme reaction will be considerably slowed down. Since the deliberation of the substrate from a cyclodextrin inclusion complex in an aqueous solution takes place instantaneously, under such circumstances the concentration of the dissolved substrates will be at the saturation value during the whole process and therefore a maximum velocity of the enzyme reaction can be achieved.

In other cases the product of an enzymatic reaction may slow down or entirely stop the conversion of the starting steroid compound, since it is adhered to the surface of the substrate or the enzyme. This effect is generally called "end product inhibition". The complexes of the substrate and the end product steroids, respectively with cyclodextrins have a different stability, due to the structural differences between the substrate and the end product. Under appropriately selected reaction conditions the steroid end product responsible for the end product inhibition can be converted into a relatively stable cyclodextrin complex without decreasing the accessability of the substrate. When the substrate forms a more stable complex with cyclodextrins than the end product, the end product inhibition can be avoided by adding the cyclodextrin to the system only at a certain stage of the reaction, when an excess amount of the end product can already be detected in the reaction medium.

Further experiments showed that the enzymatic hydrolysis of esterified steroidal molecules could be accelerated by preparing the corresponding $\alpha$- and/or $\beta$-cyclodextrin complexes. This is most probably due to a catalytic effect of the cyclodextrin molecule.

During various bioconversions it has also been observed that the formation of cyclodextrin complexes may be utilized in other ways as well. Thus for example by forming a sufficiently stable complex of a given steroid compounds, the velocity of the formation of a given isomeric structure can be decreased or the formation of a structural isomer can entirely be avoided, since the accessability of the given starting molecule is decreased.

The above-listed results can be achieved by the cyclodextrin complexes of optional compounds having a sterane structure.

The process according to the invention is illustrated by the following Examples in connection with compounds having an estrane, androstane, pregnane, cholestane or stigmastane skeleton but it is not intended to limit the application to these compounds. In the following Examples the percentage values are by weight, if not otherwise stated.

EXAMPLE 1

Substrate: hydrocortisone
Microorganism: Arthrobacter simplex (ATCC 6946)
$\alpha$-cyclodextrin; acceleration of the reaction
Introduction of the substrate: variant 1

By washing an agar culture of Arthrobacter simplex (ATCC 6946) with a physiological saline solution a suspension is prepared. By 5 ml. of the suspension the following culture medium in injected: glucose 0.3%, enzymatically hydrolysed caseine 0.5%, yeast extract 0.1%, pH=6.7. The medium is then made up to 100 ml. and sterilized in an 500-ml. Erlenmeyer flask. Cultivation is continued at 32° C. on a joggling machine having a stroke number of 230 for 18 hours, whereupon the required enzyme in induced by adding a solution of 5 mg. of hydrocortisone in 0.5 ml. of methanol. Induction is performed under the same conditions as the cultivation, for 3 hours. 50 ml. of the culture broth containing the delta-1-dehydrogenase enzyme are added into a 3-lit. Erlenmeyer flask containing 950 ml. of sterilized water and the bioconversion is carried out with the 20-fold diluted active culture obtained. As a substrate 2 g. of hydrocortisone are added in the following manner:

To the culture 20 g. of α-cyclodextrin are added. Hydrocortisone is dissolved in 20 ml. of methanol containing 10% by weight of $CaCl_2$ and the solution obtained is added to the culture containing the α-cyclodextrin. The bioconversion is carried out at 32° C. under shaking on the above machine for 5 hours. The presence of α-cyclodextrin inhibits the precipitation of the substrate in aqueous medium, and the conversion of the substrate dissolved is determined by the activity of the enzyme. In other words, the reaction velocity is higher than in the absence of cyclodextrin, when about 8 hours are required to achieve the desired conversion.

At the end of the reaction the fermentation medium contains 1920 μg./ml. of prednisolone, 40 μg./ml. of 20β-hydroxy-prednisolone and 8 μg./ml. of hydrocortisone.

EXAMPLE 2

Substrate: 17α-methyl-testosterone (androstane derivative)

Microorganism: Arthrobacter simplex (ATCC 6946)

β-cyclodextrin; elimination of the end product inhibition

Introduction of the substrate: variant 1

The culture prepared and induced as described in Example 1 is diluted to 5-fold of its original volume and a solution of 1.0 g. of 17α-methyl-testosterone in 10 ml. of methanol is added. The delta-1-dehydrogenation of 17α-methyl-testosterone is initiated. The progress of the reaction is monitored by thin layer chromatography. The substrate precipitates in the medium and dehydrogenation takes place parallel with the gradual dissolution of the substrate. When about 400 μg./ml. of delta-1-methyl-testosterone are detected, 6.0 g. of β-cyclodextrin are added to the system. The product forms an inclusion complex with the cyclodextrin and in this way the "product inhibition" effect which would result in the termination of the reaction is avoided. The stability of the cyclodextrin complex of the end product is about 5-times of that of the cyclodextrin complex of the substrate. The addition takes place in the 2nd hour of the conversion and according to the thin layer chromatography the incubation should be terminated in the 6th hour.

At the end of the conversion the culture medium contains 970 μg./ml. of delta-1-methyl-testosterone and 6 μg./ml. of methyl-testosterone.

In the absence of cyclodextrin the reaction terminates when the medium contains about 100 to 120 μg./ml. of methyl-testosterone substrate.

EXAMPLE 3

Substrate: 5-pregnene-3β,17α,21-triol-20-on-21-acetate (acylated pregnene derivative)

Microorganism: Flavobacterium lucecoloratum (NCIB 9324)

α-cyclodextrin; increase of concentration

Introduction of the substrate: variant 3

In a 750-ml. Erlenmeyer flask 200 ml. of a culture medium are injected with a slope agar culture of Flavobacterium lucecoloratum (NCIB 9324). Cultivation is performed at 30° C. on a joggling machine having a stroke number of 230 for 20 hours whereupon 5 lit. of a sterile culture medium having the same composition are injected with the culture in a laboratory fermenter. The culture medium has the following composition: yeast extract 1.0%, potassium dihydrogenphosphate 0.1%, dipotassium hydrogenphosphate 0.4%. After the injection a solution of 250 mg. of the substrate in 1.5 ml. of dimethyl formamide are added to the culture medium after sterilization by filtration. The presence of the substrate ensures the formation of the necessary enzymes during the growth of the culture. After cultivation for 12 hours the bacterium count and the enzyme activity are sufficient to start bioconversion, therefore 100 g. of 5-pregnene-3β,17α,21-trihydroxy-20-on-21-acetate are added to the culture after pretreatment with cyclodextrin. The pretreatment is performed as follows:

100 g. of the substrate are homogenized with the same amount of γ-cyclodextrin and 200 ml. of water for 20 minutes to form a rapidly soluble complex of the substrate with the cyclodextrin. The suspension obtained is added into the fermenter whereupon incubation is continued until the total amount of the substrate is consumed up (about 11 hours). Incubation is carried out at 30° C., under stirring, at 420 r.p.m. and airation at a rate of 0.5 lit./lit./min. The progress of the reaction is monitored by thin layer chromatography.

At the end of the reaction the culture contains 9020 μg./ml. of the Reichstein-S compound (4-pregnene-17α,21-dihydroxy-3,20-dione) and 30 μg./ml. of the substrate. In the absence of cyclodextrine 10 g./lit. of the substrate would have been required to obtain the desired result.

EXAMPLE 4

Substrate: 4-pregnene-17α,21-dihydroxy-3,20-dione-17-acetate (acylated corticosteroid)

Microorganism: Curvularia prasadii (IMI 71475)

β-cyclodextrin; catalyzation of exter hydrolysis

Introduction of the substrate: variant 1

In a 500-ml. Erlenmeyer flask by a suspension of spores washed off from a slope agar culture of Curvularia prasadii (IMI 71475) 100 ml. of a culture medium are injected. The culture medium has the following composition: soya flour 1.0%, corn steep liquor 0.3%, corn starch 0.3%, malt extract 0.5%, pH=6.2. Cultivation is performed at 26° C. for 24 hours, whereupon in a 500-ml. Erlenmeyer flask 100 ml. of a culture medium prepared without malt extract but otherwise having the same composition as given above are injected with 10 ml. of the culture obtained. The culture is shaken at 26° C. and to the 16-hour culture which is still growing 0.12 g. of the 4-pregnene-17α,21-dihydroxy-3,20-dione-17-acetate substrate in 3 ml. of methanol are added. During a further incubation period the substrate is hydroxylated in the 11β-position to give hydrocortison-17-acetate. According to thin layer chromatography in the 20th hour of the conversion the culture contains 10% of unreacted substrate. At this stage 0.96 g. of β-cyclodextrin are added to the system. Cyclodextrin has a catalytic effect on the enzymatic hydrolysis of the acetyl group of the steroid molecule, therefore in the subsequent phase of bioconversion in addition to hydroxylation, which is slowed down, the acetyl group is splitted off. After about 3 hours the reaction is terminated.

At the end of the conversion the fermentation medium contains 0.730 μg./ml. of hydrocortisone (4-pregnen-11β,17α,21-trihydroxy-3,20-dione), 0.185 μg./ml. of hydrocortison-17-acetate, 0.005 μg./ml. of Reichstein-S-17-acetate and 0.040 μg./ml. of Reichstein-S compound.

EXAMPLE 5

Substrate: hydrocortisone
Microorganism: Arthrobacter simplex (ATCC 6946)
β-cyclodextrin; acceleration of the reaction
Introduction of the substrate: variant 2

By 30 ml. of a suspension obtained washing off a culture of Arthrobacter simplex grown on a solic culture medium 5 lit. of a sterilized culture medium are injected in a laboratory fermenter. The culture medium has the following composition: glucose 0.3%, peptone 0.3%, yeast extract 0.1%, pH=6.8. The cultivation is carried out at 35° C., under stirring at 240 r.p.m. with a 0.5 lit./lit./min. airation for 20 hours. By 1 lit. of the culture 9 lit. of a sterilized culture medium are injected in a laboratory fermenter. The latter culture medium has the following composition: glucose 0.5%, peptone 0.5%, yeast extract 0.4%, pH=6.8. Cultivation is performed at 35° C., with stirring at 600 r.p.m. and a 0.3 lit./lit./min. airation for 18 hours. Thereafter a solution of 0.5 g. of hydrocortisone in 50 ml. of methanol are added to induce the formation of the enzyme. After incubation for four hours the active culture is passed into an acid-resistant equipment in which the medium of the bioconversion has previously been prepared.

Medium: Into the equipment 90 lit. of tap water and 1200 g. of β-cyclodextrin are added, the equipment is heated up to 100° C. and the medium is sterilized at this temperature for 20 minutes, whereupon it is cooled to 35° C. 1.0 g. of 2-methyl-1,4-naphthoquinone and 400 g. of hydrocortisone are dissolved in 4 lit. of methanol containing 400 g. of $CaCl_2$. The solution is sterilized by filtration and is added into the equipment. Simultaneously with the addition the bioconversion is started. During the conversion practically the total amount of the steroid substrate is dissolved and therefore there is no risk of the formation of a mixed crystal when the product precipitates.

The bioconversion medium is incubated at 35° C., under stirring at 180 r.p.m. with a 0.6 lit./lit./min. reaction. The progress of the reaction is monitored by thin layer chromatography and the reaction is terminated as soon as the amount of the substrate decreases the 2.0% by weight. The fermentation medium is then extracted with ethyl acetate twice, in counterflow. The extract is concentrated in vacuo, at a temperature up to 40° C. to a concentration of 8 g./lit. (about 50 lit. of a first concentrate), decolored with a mixture of 40 g. of activated carbon and 100 g. of Celite and evaporation is continued until crystallization takes place (about 2 lit.). The suspension is cooled to 5° to 10° C., and filtered after standing for several hours. The mother liquor is treated with a five-fold amount of diisopropyl ether, cooled and the precipitated product is filtered off.

375 g. of a product having the following characteristics are obtained:
 purity: 98% by weight
 drying loss: 1% by weight
 sulfate ash: 0.1% by weight
 hydrocortisone residue: 1.2% by weight
 other steroids: 0.35% by weight
 melting point: 234° to 236° C.
 $[\alpha]_D^{20} = +98°$ (dioxane, c=1).

To recover β-cyclodextrin the extract is stirred with 1 lit. of cyclohexane at 18° to 20° C., for one hour. The precipitate obtained is filtered off, suspended in about one lit. of water and cyclohexane is eliminated by steam distillation, under boiling. The aqueous β-cyclodextrin suspension is allowed to stand at 5° to 10° C. overnight, the crystals are filtered off and dried in vacuo. About 700 g. of β-cyclodextrin are recovered and can be used for further operations.

EXAMPLES 6 to 11

The following microbiological conversions are carried out following the procedures described in the previous Examples, under the given reaction conditions, using cyclodextrin to intensificate the reactions.

EXAMPLE 6

Substrate: sitosterine
Microorganism: Mycobacterium sp. (NRRL β-3805)
β-cyclodextrin; increase of the concentration
Introduction of the substrate: variant 1
End product: androstat-4-diene-3,17-dione The side-chain of the substrate is decomposed according to Marscheck, W. J. Kraychi and Muir R. D. (1972) Appl. Microbiol. 23, 72. The steroid to cyclodextrin molar ratio is 1:0.2. The culture medium contains 0.5% of $Na_2HPO_4.7H_2O$. In the presence of cyclodextrin the sitosterine concentration can be increased up to 2 g./lit. while in the absence of cyclodextrine only a concentration of 1 g./lit. can be achieved (conversion time: 170 hours in both cases).

EXAMPLE 7

Substrate: progesterone
Microorganism: Ophiobolus herpotrichus
β-cyclodextrin; completion of the conversion
Introduction of the substrate: variant 1
En product: 21-dihydroxy-progesterone The process is carried out according to Meystre et al., Helv. Chim. Acta 37, 1548 (1954). The steroid to cyclodextrin molar ratio is 1:0.2. The microorganism is cultivated on a beer mash medium for 3 days, whereupon an acetonic solution of the progesterone substrate is added up to a concentration of 0.25 g./lit. of fermentation broth. Without the use of cyclodextrin the bioconversion lasts three days longer and the amount of the substrate residue is about 25%. If about 24 to 30 hours before starting the bioconversion β-cyclodextrin is added to the reaction mixture, the amount of the substrate residue is considerably reduced.

EXAMPLE 8

Substrate: 4-pregnene-17α,21-dihydroxy-3,20-dione (Reichstein-S)
Microorganism: Curvularia Lunata (IFO 49)
β-cyclodextrin; influence of the ratio of the reaction products
Introduction of the substrate: variant 1
Main product: hydrocortisone The reaction is essentially carried out according to Kondo, E. and Mitsugi, T., J. Agrc. Chem. Soc. Japan 35, 521 (1961). The steroid to cyclodextrin molar ratio amounts to 1:0.3. Without using cyclodextrin as a result of bioconversion 35 to 40% by weight of 6β-hydroxy-Reichstein-S, 15 to 20% by weight of 14α-hydroxy-Reichstein-S, 3 to 5% by weight of 11α-hydroxy-Reichstein-S and about 5% by weight of 7,14α-dihydroxy- and 5% by weight of 6β,14α-dihydroxy-Reichstein-S are obtained. If at the start of the bioconversion β-cyclodextrin is added to the mixture in the above ratio, the proportion of the 11α-hydroxy-Reichstein-S (epihydrocortisone) can be increased to about twice of the above amount.

EXAMPLE 9

Substrate: 16α-methyl-Reichstein-S
Microorganism: Curvularia lunata (ATCC 12017)
β-cyclodextrin; increase of the conversion grade
Introduction of the substrate: variant 1
End product: 11β,17α,21-trihydroxy-16α-methyl-pregn-4-ene-3,20-dione(16α-methyl-hydrocortisone)

The reaction is essentially performed according to Canonica, L. et al., Gass. Chim. Ital. 93, 368 (1963). The steroid to cyclodextrin molar ratio is 1:1. In the absence of cyclodextrin the desired end product is obtained in an amount of about 55% by weight. If at the start of the bioconversion β-cyclodextrin is added to the mixture in the above ratio, the proportion of the end product in the reaction mixture is increased by about 5 to 10%.

EXAMPLE 10

Substrate: 3β,17α,21-trihydroxy-pregn-5-en-21-acetate
Microorganism: Flavobacterium dehydrogenans (ATCC 13930)
β-cyclodextrin; increase of concentration
Introduction of the substrate: variant 1
End product: Reichstein-S The reaction is essentially carried out according to the U.S. Pat. No. 3,009,936. The steroid to cyclodextrin molar ratio amounts to 1:0.3. By using cyclodextrin the concentration can be increased to twice of the amount obtained without the use of cyclodextrin.

EXAMPLE 11

Substrate: Lanatoside-A (digitalis glucoside)
Microorganism: Streptomyces purpurascens
β-cyclodextrin; increase of the concentration
Introduction of the substrate: variant 1

The reaction is carried out according to the Hungarian patent specification No. 176 250. The Lanatoside-A to cyclodextrin molar ratio amount to 1:1. For comparison without the use of cyclodextrin an organic solution containing 0.5 g./lit. of Lanatoside-A is added to a two days culture of Streptomyces purpurascens. If after cultivation of the microorganism for 2 days, at the start of the bioconversion β-cyclodextrin is added to the reaction mixture in the above ratio, the concentration of the substrate can be increased up to 2.0 g./lit.

We claim:

1. A process for the intensification of a microbiological conversion of a steroid product which comprises the step of microbiologically converting the steroid substrate wherein the steroid is selected from the group consisting of an estrane, androstane, pregnane, cholestane, stigmastane and cardenolide, in the presence of an alpha-, beta- or gamma-cyclodextrin or a mixture thereof by using 0.2 to 3 moles of the cyclodextrin per mole of the steroid substrate.

2. The process defined in claim 1 which further comprises recovering the cyclodextrin from the reaction mixture after termination of the reaction to form the steroid product.

3. The process defined in claim 1, which comprises adding the cyclodextrin to the reaction mixture before or at the beginning of the microbiological reaction.

4. The process defined in claim 1, which comprises adding the cyclodextrin to the reaction mixture before the microbiological reaction.

5. The process defined in claim 1, which comprises adding an inclusion complex of the steroid substrate and a cyclodextrin to the reaction mixture.

6. The process defined in claim 5, which comprises using a solution or suspension of an inclusion complex of the steroid substrate and the cyclodextrin.

7. The process defined in claim 1, which comprises adding the cyclodextrin to the reaction mixture at a conversion grade of 35–50%.

8. The process defined in claim 1, which comprises sterilizing the cyclodextrin, an inclusion complex of the cyclodextrin and the steroid substrate or a solution thereof before addition into the bioconversion medium.

9. The process defined in claim 1, which comprises sterilizing the cyclodextrin added to the bioconversion medium together with the medium.

10. The process defined in claim 2, which comprises extracting the steroid product with an organic solvent from an aqueous bioconversion medium and from the raffinate precipitating the cyclodextrin, by the addition of a solvent to decrease the solubility of the cyclodextrin, and subsequently filtering off the cyclodextrin.

11. The process defined in claim 1 wherein the steroid substrate is a pregnane selected from the group consisting of hydrocortisone, 5-pregnene-3beta-17alpha,21-triol-20-one-21-acetate, Reichstein S-17-acetate, progesterone, Reichstein S, 16alpha-methyl-Reichstein S, and 3beta, 17alpha,21-trihydroxy-pregn-5-ene-21-acetate.

12. The process defined in claim 1 wherein the steroid substrate is 17-alpha-methyl testosterone.

13. The process defined in claim 1 wherein the steroid substrate is sitosterine.

14. The process defined in claim 1 wherein the microbiological conversion of the steroid substrate to the steroid product is carried out in an aqueous medium.

* * * * *